United States Patent [19]

Cohen et al.

[11] 4,138,880
[45] Feb. 13, 1979

[54] VAPOR EMISSION RECOVERY AND MEASURING METHOD AND VAPOR RECOVERY COLLECTION BOOT

[75] Inventors: Jules B. Cohen, Lakewood, Colo.; Peter P. Principe, Columbia, Md.

[73] Assignee: The United States of America as represented by the Administrator of the U.S. Environmental Protection Agency, Washington, D.C.

[21] Appl. No.: 801,443

[22] Filed: May 27, 1977

[51] Int. Cl.$^2$ ............................................ G01N 31/00
[52] U.S. Cl. ............................................ 73/23; 141/93
[58] Field of Search ................... 73/23; 141/7, 52, 59, 141/311, 392, 93

[56] References Cited

U.S. PATENT DOCUMENTS

| | | | |
|---|---|---|---|
| 3,543,484 | 12/1970 | Davis | 141/52 |
| 3,566,671 | 3/1971 | Blum et al. | 73/23 |
| 3,710,830 | 1/1973 | Gilson | 141/93 |
| 3,783,911 | 1/1974 | Husa et al. | 141/11 |
| 3,830,267 | 8/1974 | Cass | 141/52 |
| 3,881,894 | 5/1975 | Onufer | 141/93 |
| 3,993,112 | 11/1976 | Weidenaar et al. | 141/392 |

Primary Examiner—Stephen A. Kreitman
Attorney, Agent, or Firm—Browdy and Neimark

[57] ABSTRACT

A testing method and apparatus for use at service stations to establish whether gasoline refueling systems meet government regulations for gasoline vapor emission. The apparatus includes a boot used to surround a gasoline dispensing nozzle while delivering gasoline to an automobile gas tank. The boot is of flexible material and has a hollow wall defining a vapor collection chamber, the inner part of the hollow wall having apertures distributed over its surface to allow gasoline vapor to be drawn into the chamber by suction. The outer part of the hollow wall has a stub connectable to a tube leading to vapor emission analyzing equipment. In the method, such a boot is used to recover the emitted vapors directly from the vehicle-nozzle interface region and the recovered vapors are drawn by a pump through a flow meter and delivered to an analyzer. The outputs of the flow meter and analyzer may be delivered to a computing device to determine the mass emission rate of hydrocarbons and the accumulated total hydrocarbon mass emitted.

14 Claims, 6 Drawing Figures

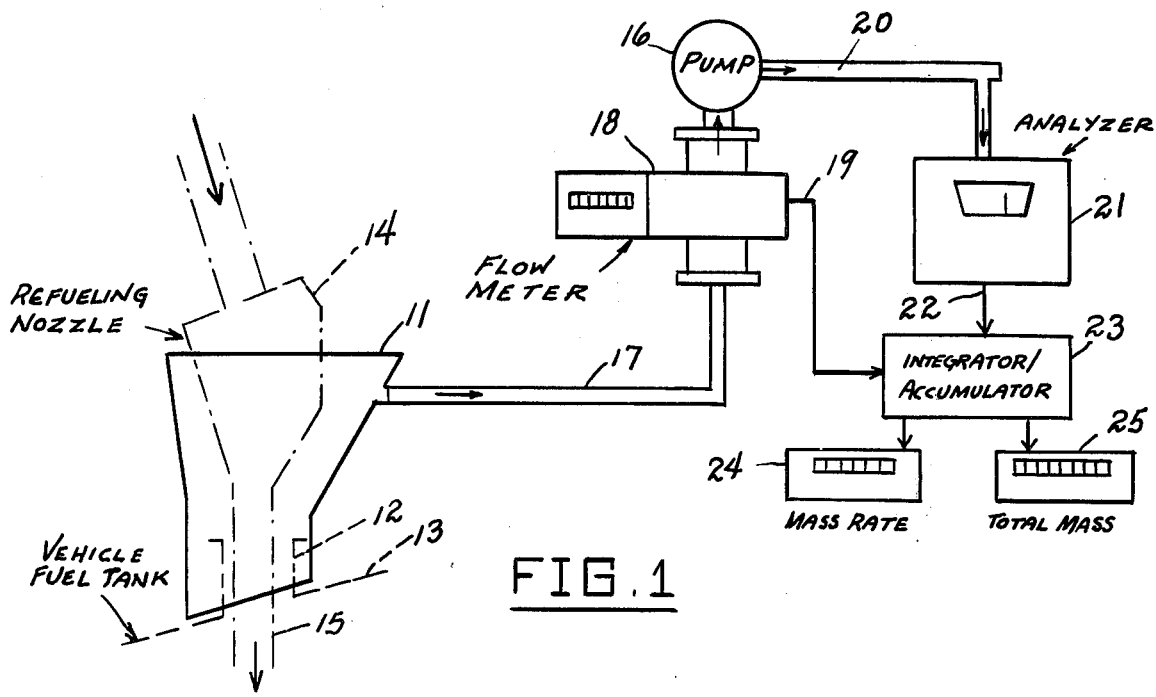
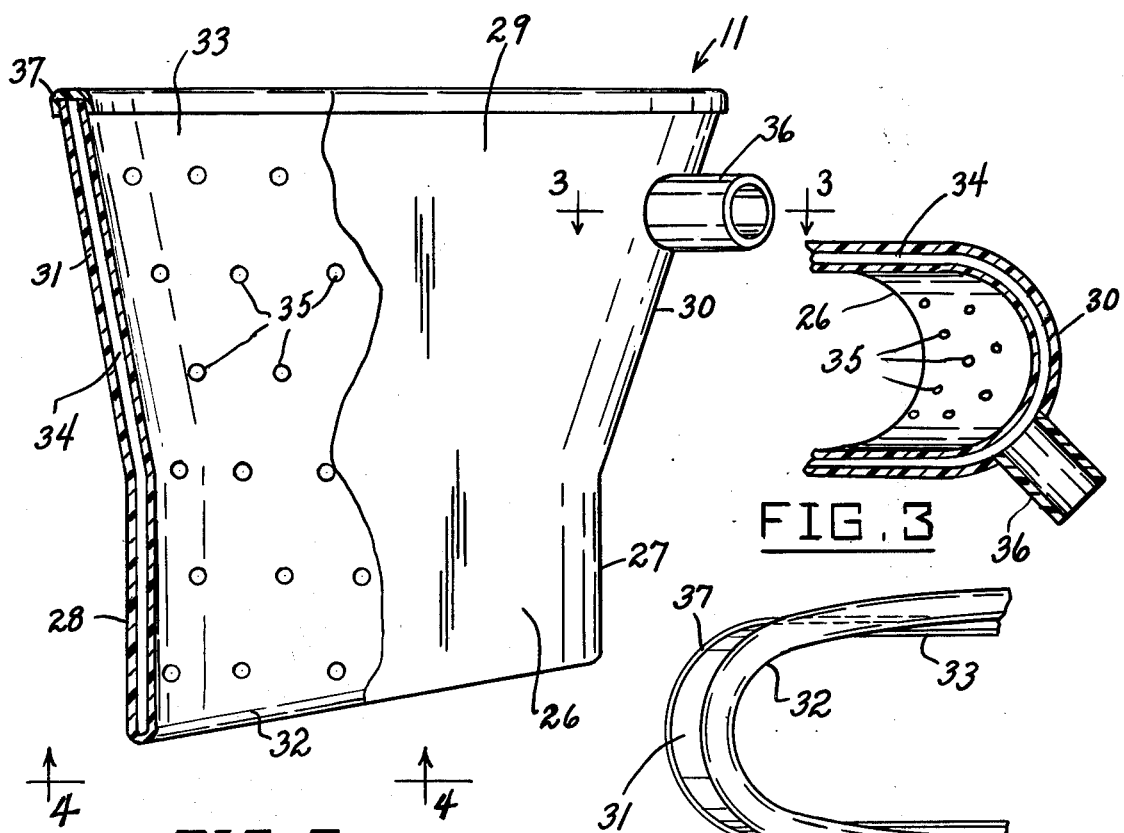

VAPOR EMISSION RECOVERY AND MEASURING METHOD AND VAPOR RECOVERY COLLECTION BOOT

FIELD OF THE INVENTION

This invention relates to methods and apparatus for measuring gas and vapor emission, and more particularly to methods and apparatus for collecting gasoline vapors at gasoline service stations to determine whether the refueling systems at said stations meet government regulations for mass emission limitations.

BACKGROUND OF THE INVENTION

The U.S. Environmental Protection Agency is responsible for establishing limitations on vapor emission at gasoline refueling service stations. In order to determine whether the refueling systems meet these limitations, it is necessary to employ apparatus for collecting gasoline vapors emitted at the dispensing nozzles during gasoline refueling and for measuring and displaying the amount of emission. Various test procedures and equipment for this purpose have been proposed in the Federal Register (40 FR 197, Oct. 9, 1975), all of which have proved to be too complex and costly for the results obtained. For example, some previously proposed procedures have involved the use of specially modified nozzles, carbon adsorption devices, and other cumbersome and expensive equipment. In general, the previously proposed apparatus and procedures have been found to be unsatisfactory because they require an excessive amount of manpower, require a longer period of time to run the required tests, and involve the use of excessive amounts of equipment.

SUMMARY OF THE INVENTION

Accordingly, a main object of the invention is to provide a novel and improved method and apparatus for collecting gasoline vapors at gasoline refueling service stations in order to establish whether the refueling systems at the stations meet government regulations for mass emission limitations.

A further object of the invention is to provide an improved gasoline vapor collecting and measuring method which provides accurate and reproducible data, which requires less manpower than previously proposed processes for the desired purpose, which provides a direct measurement of mass emissions resulting from vapor losses at the fill necks of the tanks of vehicles being refueled, which collects the vapor without introducing undesired pressure differentials, and which provides most immediate results, whereas prior methods require several days to provide like results.

A still further object of the invention is to provide a novel and improved vapor collection apparatus which employs relatively simple components, which can be readily positioned around the filling neck of a gasoline tank with little effort and can receive the gasoline refueling nozzle so as to directly draw in most of the vapor liberated during the refueling process, thereby enabling accurate direct measurements to be made of the vapor emissions.

A still further object of the invention is to provide an improved gasoline vapor collection boot adapted to be easily placed around the neck of a motor vehicle gasoline tank and shaped so as to receive a gasoline dispensing nozzle and allow the nozzle to be inserted in the neck for delivery of gasoline to the tank, the boot being hollow and forming a vapor collection chamber surrounding the region around the nozzle and being apertured over its inner surface area to convey the liberated gasoline vapor into the collection chamber, from which it can be conveyed by suction to analyzer apparatus for measuring and indicating the emission, the boot being relatively compact in size and light in weight so that it is easy to handle, and being pliable so that it can readily conformably receive dispensing nozzles of different shapes and operate effectively therewith.

BRIEF DESCRIPTION OF THE DRAWINGS

Further objects and advantages of the invention will become apparent from the following description and claims, and from the accompanying drawings, wherein:

FIG. 1 is a schematic block diagram of a typical gasoline vapor emission measuring apparatus according to the present invention.

FIG. 2 is an enlarged elevational view, partly in vertical cross-section, of a vapor collection boot according to the present invention, as employed in the apparatus of FIG. 1.

FIG. 3 is a horizontal cross-sectional view taken substantially on the line 3—3 of FIG. 2.

FIG. 4 is a fragmentary bottom view of the collection boot, taken substantially on line 4—4 of FIG. 2.

DESCRIPTION OF A PREFERRED EMBODIMENT

Figure 5:
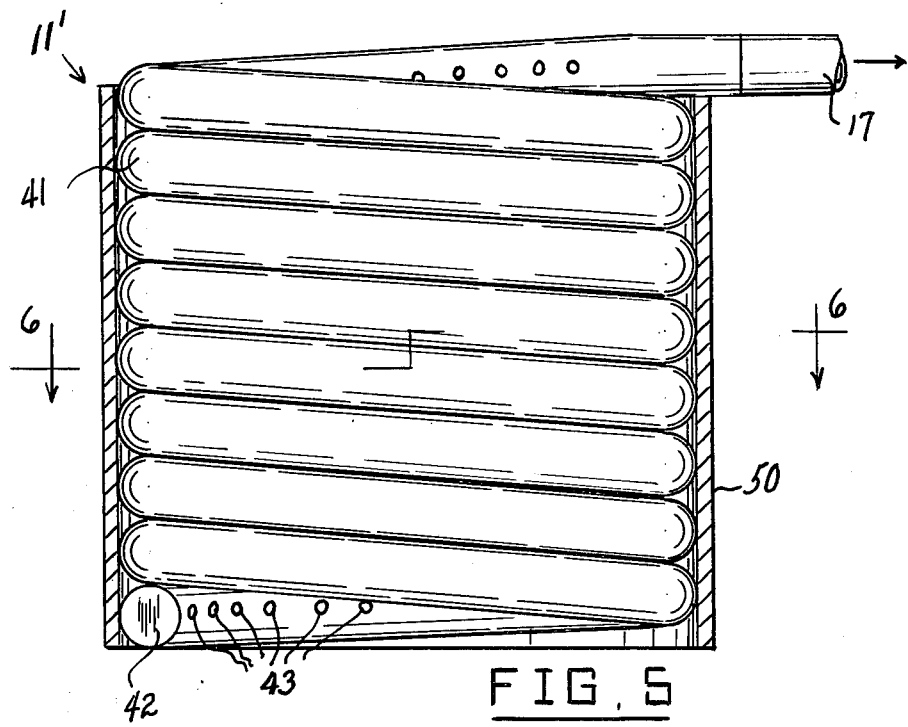
FIG. 5 is an enlarged elevational view similar to FIG. 2 but showing another form of vapor collection boot according to the present invention, employing helically wound tubing with inwardly facing perforations.

Referring to the drawings, and more particularly to FIG. 1, a typical arrangement of testing apparatus as contemplated by the present invention comprises a hollow-walled vapor collection boot 11 engageable over the filler neck 12 of an automobile gas tank 13 and arranged to receive a refueling nozzle 14, with the discharge spout 15 of the nozzle extending through the neck 12, as shown in dotted view. The boot 11 is shaped to surround the interface region between the refueling nozzle and the gas tank neck, and is constructed, as will be presently described, so as to collect the gasoline vapor liberated during the refueling process. Thus, the boot cavity is connected at its upper portion by a conduit 17 through a conventional gas flow meter 18 to the intake of a pump 16. The gas flow meter 18 is preferably a turbine meter or flow meter of the positive-displacement type providing an electrical output signal at its output line 19 representing the volumetric flow rate through the meter.

The outlet conduit 20 of pump 16 is connected to the inlet of a conventional gas analyzer 21, such as a Horiba Model PIR-2000 nondispersive infrared (NDIR) gas analyzer or the like, providing an electrical output signal at its output line 22 representing the concentration of the hydrocarbon gas sensed by the analyzer (for example, in percent hydrocarbon) per unit of time.

The flow rate signal in the line 19 and the sensed concentration signal in the line 22 are furnished as inputs to an integrator/accumultor 23, which is a computing device which integrates the area under the hydrocarbon concentration/time curve in one second intervals. Using the input from the meter 18 and a constant, and computing device 23 determines the mass emission rate of hydrocarbons and displays it digitally on a display device 24. The mass is accumulated by a counter in the computing apparatus and is displayed digitally on a display device 25; at the end of the test, when the mass emission rate (from display device 24) is zero, the total accumulated hydrocarbon mass emitted can be read off the counter display device 25. This number, corrected for temperature and barometric pressure, can be divided by the number of gallons pumped to yield the mass emission rate in grams per gallon. The temperature and pressure corrections can be made either manually or may be programmed into the computer device so that only the division has to be performed to obtain the grams per gallon emitted.

Referring to FIGS. 2, 3 and 4, the vapor collection boot 11 comprises a hollow-walled longitudinally elongated sleeve-like member of suitable durable pliable material, such as polyvinyl chloride (PVC), whose lower part 26 has vertical semi-cylindrical end portions 27 and 28 and whose upper part 29 has upwardly diverging arcuately curved end portions 30 and 31. The top rim of the boot comprises a downwardly facing channel element 37 sealingly secured on and receiving the top peripheral edges of the inner and outer wall elements of the boot. The front and rear hollow walls of the upper part are normally substantially parallel, whereas the front and rear hollow walls of the lower part are outwardly convex, so that the lower mouth 32 of the boot is normally substantially oval in shape, as shown in FIG. 4, whereas the upper mouth 33 is substantially normally parallel-sided. The plane of the lower mouth 32 is inclined to the horizontal, as viewed in FIGS. 1 and 2, to facilitate placement and support of the boot around the neck 12 of the vehicle gas tank, since the surface around the neck is usually so inclined. The pliable and yieldable nature of the material forming the boot allows a wide range of nozzles 14 of varying shapes to be readily introduced into the boot.

As above mentioned, boot 11 is "longitudinally elongated," namely, has front and rear walls which are relatively wide horizontally, as viewed in FIG. 2, as compared to the distance between said walls.

The inner and outer wall elements of the hollow-walled boot define a collection space 34 therebetween. The inner wall element is formed with apertures 35 distributed over its surface to allow air and liberated gasoline vapor to be freely drawn into the collection space 34.

The upper part 29 of the boot is provided with an outwardly projecting conduit element 36 communicating with space 34, which is connected to the suction conduit 17 for inducing the collection of the liberated hydrocarbon vapor by the boot.

With the boot connected to the suction conduit 17, as shown in FIG. 1, and positioned and held around the neck 12, the hydrocarbon emission during refueling will be measured by the apparatus in the manner above described, the boot 11 acting to directly collect the liberated hydrocarbon vapor at the interface region between the nozzle 14 and the neck 12 with minimal escape of the emission vapor to the atmosphere and with only a limited admixture of atmospheric air.

If so desired, the output of the analyzer 21 may be delivered directly to a conventional chart recorder so as to obtain a recorded curve representing the varying hydrocarbon emission occurring during a refueling procedure. The information provided by such a curve may be used in determining the total emission, and this value may be divided by the number of gallons pumped, to yield the mass emission rate.

As above mentioned, the generally upwardly flaring shape of the boot 11 and the pliability of the material of the boot make it possible to accommodate a wide range of shapes of gasoline dispensing nozzles. The top cover channel element 37 provides a sufficient stiffening effect to maintain the normal longitudinally elongated shape of the boot.

While the boot 11 shown in FIGS. 2 to 4 has a "longitudinally elongated" cross-sectional shape, it will be understood that this shape is optional and that any other desired cross-sectional shape may be employed as long as a refueling nozzle can be inserted therein.

Figure 6:
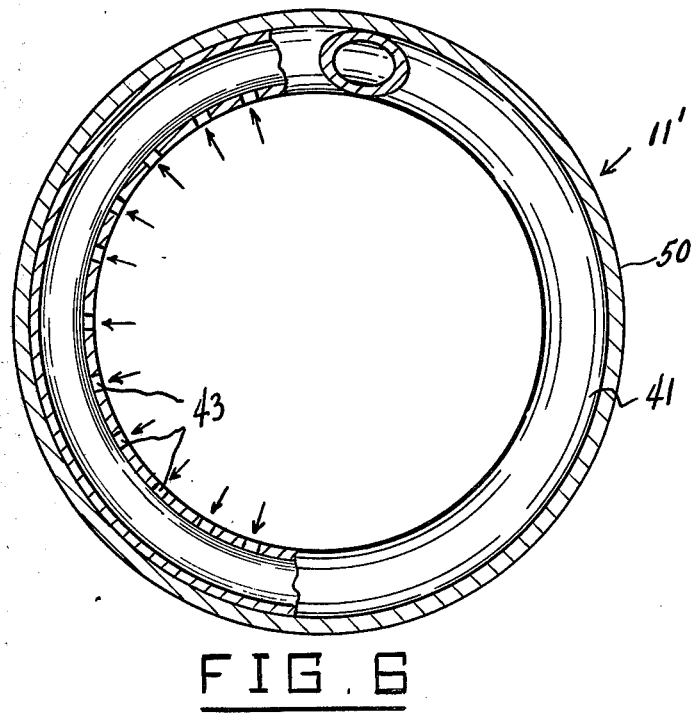
FIG. 6 is a horizontal cross-sectional view taken substantially on line 6—6 of FIG. 5.

In the embodiment illustrated in FIGS. 5 and 6, the boot, shown at 11', comprises helically coiled tubing 41 forming a generally cylindrical sleeve-like member or enclosure adapted to be placed over a gas tank filler neck 12 in a manner similar to that above described, and to receive a standard refueling nozzle 14, as in FIG. 1. The bottom end of the coiled tubing 41 is closed off, as shown at 42, and the top end thereof is connected to the conduit 17 in a system similar to that shown in FIG. 1. The coiled tubing 41 is formed with perforations 43 facing inwardly to allow liberated gasoline vapor from the interface region between the refueling nozzle and the gas tank neck to be drawn into the helical chamber defined by the coiling tubing and to be transferred to the conduit 17 by the suction induced by pump 16. While the cross-sectional shape of the coiled tubing boot 11 is shown as being circular, as in the first-described boot 11, the cross-sectional shape is optional. The coiled tubing 41 may be supported by means of a felxible sleeve 50 or the like surrounding it.

While a specific embodiment of an improved vapor recovery collection system and method, and boots for use therein, in determining the mass emission rate of hydrocarbons have been disclosed in the forgoing description, it will be understood that various modifications within the scope of the invention may occur to those skilled in the art. Therefore, it is intended that adaptations and modifications should and are intended to be comprehended within the meaning and range of equivalents of the disclosed embodiments.

What is claimed is:

1. A boot for use in a testing apparatus to measure vapor emission from the interface region between a dispensing nozzle and the neck of a liquid storage container, said boot being adapted to be placed over the container neck and to surround and receive the nozzle without being connected in sealed engagement therewith, said boot comprising a sleeve-like member, open at both ends, having a hollow peripheral wall defining a vapor collection chamber, said hollow wall comprising an inner wall element and an outer wall element, the inner wall element being provided with holes substantially uniformly distributed over the surface area thereof, and conduit receiving means for permitting a conduit to connect with the boot to convey collected vapor from said collection chamber to an analyzing means.

2. The boot of claim 1, and wherein said conduit receiving means comprises a conduit receiving element communicatively connected to and extending through said outer wall element.

3. The boot of claim 1, and wherein said sleeve-like member comprises pliable material adapted to conform generally to the shape of a nozzle received therein.

4. The boot of claim 3, and wherein said inner and outer wall elements comprise sheets of said pliable material the surfaces of which are spaced essentially equidistant along substantially all points.

5. The boot of claim 4, and wherein said inner and outer sheets comprise a single sheet folded upon itself at one end of the boot.

6. The boot of claim 1, and wherein said sleeve-like member comprises relatively thin pliable polyvinyl chloride.

7. The boot of claim 1, and wherein said sleeve-like member has front and rear walls which are relatively wide as compared to the distance therebetween.

8. The boot of claim 1, and wherein said sleeve-like member has front and rear walls which are relatively wide as compared to the distance therebetween and flare in width toward one open end of the sleeve-like member.

9. The boot of claim 8, and wherein said one end of the sleeve-like member comprises a peripherally extending cover element sealingly secured over the edges of the inner and outer wall elements and acting as a stiffener.

10. The boot of claim 8, and wherein said front and rear walls of said one end of the sleeve-like member are normally substantially parallel and the other open end of the sleeve-like member is generally oval.

11. The boot of claim 8, and wherein the plane of the mouth of the other open end of the sleeve-like member, opposite said one end, is inclined relative to the plane of the mouth of said one end of the sleeve-like member.

12. The boot of claim 1, and wherein one end of the sleeve-like member comprises a peripherally extending channel element receiving and being sealingly secured to the edges of the outer and inner wall elements at said one end and acting as a stiffener.

13. A method of directly measuring the amount of gasoline vapor emitted to the atmosphere during refueling operations, comprising forming a non-sealing enclosure around the interface region of a gasoline dispensing nozzle and the neck of a gasoline tank receiving said nozzle during refueling, collecting the liberated vapor from said enclosure by applying suction thereto, said suction being substantially uniformly distributed over the inside surface area of the enclosure, and measuring the mass of the liberated vapor collected from the enclosure.

14. The method of claim 13, and wherein said enclosure is formed by placing a boot over the neck of the gasoline tank and inserting a nozzle thereinto such that the nozzle is surrounded in a non-sealing manner by said boot, said boot comprising a sleeve-like member having a hollow peripheral wall defining a vapor collection chamber, said hollow wall comprising an inner wall element and an outer wall element, the inner wall element being provided with holes distributed thereover, and conduit receiving means for permitting a conduit to connect with the boot to convey collected vapor from said collection chamber to a measuring means.

* * * * *